United States Patent
Fujino et al.

(10) Patent No.: US 6,962,998 B2
(45) Date of Patent: Nov. 8, 2005

(54) PROCESSES FOR PRODUCING RACEMIC PIPERIDINE DERIVATIVE AND FOR PRODUCING OPTICALLY ACTIVE PIPERIDINE DERIVATIVE

(75) Inventors: Toshihiro Fujino, Kuwana (JP); Haruyo Sato, Nagoya (JP)

(73) Assignee: Toray Industries, Inc. (JP)

( * ) Notice: Subject to any disclaimer, the term of this patent is extended or adjusted under 35 U.S.C. 154(b) by 315 days.

(21) Appl. No.: 10/296,772

(22) PCT Filed: Jun. 4, 2001

(86) PCT No.: PCT/JP01/04689

§ 371 (c)(1),
(2), (4) Date: Dec. 13, 2002

(87) PCT Pub. No.: WO01/96301

PCT Pub. Date: Dec. 20, 2001

(65) Prior Publication Data

US 2003/0130313 A1 Jul. 10, 2003

(30) Foreign Application Priority Data

Jun. 14, 2000 (JP) ........................................ 2000-178117
Sep. 18, 2000 (JP) ........................................ 2000-282512

(51) Int. Cl.⁷ ...................... C07D 211/10; C07D 211/14
(52) U.S. Cl. ...................... 546/236; 546/215; 546/225; 546/226; 546/227; 546/228; 546/237; 546/238
(58) Field of Search ................................ 546/216, 225, 546/226, 227, 228, 236, 237, 238

(56) References Cited

FOREIGN PATENT DOCUMENTS

| JP | 63-185943 | 8/1988 |
|---|---|---|
| JP | 06-135906 | 5/1994 |
| WO | 96/09290 A1 | 3/1996 |

OTHER PUBLICATIONS

Clas Sonesson et al., "An Efficient Synthesis of the Novel Dopamine Autoreceptor Antagonist S–(–)–OSU6162, via Palladium Catalyzed Cross–Coupling Reaction," *Tetrahedron Letters*, (1994), vol. 35, No. 48, pp. 9063–9066.

Hans Malmberg et al, Lithium Methylorganocuprates Containing Chiral 2–(N–Methyl–2–pyrrolidinyl)–, 2–(N–Methyl–2–piperidinyl)–or 2–(1–N,N–Dimethylaminoethyl)–phenyl Groups. A Comparison of Addition to Two Acyclic Enones, *Acta Chemica Scandinavica B 35*, (1981), pp. 625–629.

Sonesson, C. et al, "Substituted (S)–Phenylpiperidines and Rigid Congeners as Preferential Dopamine Autoreceptor Antaagonists: Synthesis and Structure–Activity Relationships, " *J. Med. Chem.*, 1994, vol. 37, pp. 2735–2753.

*Primary Examiner*—Patricia L. Morris
(74) *Attorney, Agent, or Firm*—Piper Rudnick LLP

(57) ABSTRACT

Disclosed are a method for producing racemic piperidine derivatives by processing optically-active piperidine derivatives in a hydrogen atmosphere in the presence of a reducing catalyst; and a method for producing optically-active piperidine derivatives or their acid salts by optically resolving the racemic piperidine derivatives obtained in the former method.

6 Claims, No Drawings

PROCESSES FOR PRODUCING RACEMIC PIPERIDINE DERIVATIVE AND FOR PRODUCING OPTICALLY ACTIVE PIPERIDINE DERIVATIVE

TECHNICAL FIELD

The present invention is to provide a method for producing racemic piperidine derivatives by racemizing unnecessary optical antipodes, by-products of optical resolution to give optically-active piperidine derivatives of general formulae (1), (2) and (3):

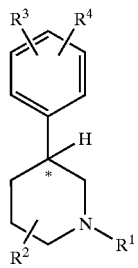

(1)

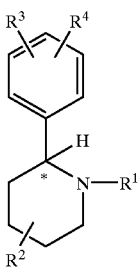

(2)

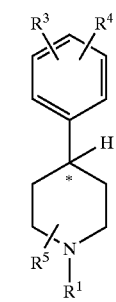

(3)

wherein $R^1$ represents a lower alkyl group having from 1 to 4 carbon atoms, a phenyl group, or an aralkyl group; $R^2$, $R^3$ and $R^4$ may be the same or different, each representing a hydrogen atom, an alkyl group, a phenyl group, an aralkyl group, an alkoxycarbonyl group, an alkylsulfonyl group, an arylsulfonyl group, an aralkylsulfonyl group, or an acyl group; $R^5$ represents an alkyl group, a phenyl group, an aralkyl group, an alkoxycarbonyl group, an alkylsulfonyl group, an arylsulfonyl group, an aralkylsulfonyl group, or an acyl group.

The optically-active piperidine derivatives are useful for medicines and their intermediates. In particular, hydrochloride of optically-active 3-[3-(methylsulfonyl)phenyl]-1-propylpiperidine hydrochloride salt of formula (6) is a compound useful for medicines for Parkinson's disease.

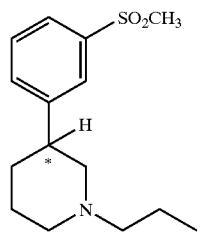

(6)

BACKGROUND ART

For obtaining optically-active piperidine derivatives, their racemates may be subjected to optical resolution. However, its theoretical yield is 50% of the racemates, and the process is unsatisfactory for industrial use. Therefore, if unnecessary optical antipodes could be racemized and recycled for the starting materials for optical resolution, the yield of the intended optically-active piperidine derivatives would be approximately 100% in theory. Accordingly, racemization of optically-active piperidine derivatives to give racemic piperidine derivatives is an important technique. However, no one knows at all a method for racemizing optically-active piperidine derivatives of general formulae (1), (2) and (3):

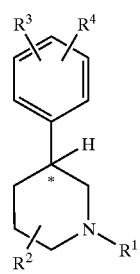

(1)

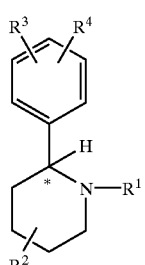

(2)

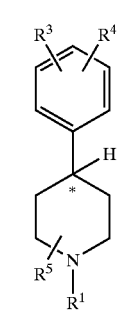

(3)

wherein $R^1$ represents a lower alkyl group having from 1 to 4 carbon atoms, a phenyl group, or an aralkyl group; $R^2$, $R^3$ and $R^4$ may be the same or different, each representing a hydrogen atom, an alkyl group, a phenyl group, an aralkyl group, an alkoxycarbonyl group, an alkylsulfonyl group, an arylsulfonyl group, an aralkylsulfonyl group, or an acyl group; $R^5$ represents an alkyl group, a phenyl group, an aralkyl group, an alkoxycarbonyl group, an alkylsulfonyl group, an arylsulfonyl group, an aralkylsulfonyl group, or an acyl group.

On the other hand, for producing optically-active 3-[3-(methylsulfonyl)phenyl]-1-propylpiperidine, for example, known are a method of deriving it from optically-active 3-(3-hydroxyphenyl)-1-propylpiperidine (*J. Med. Chem.*, 1994, 37, 2735–2753); and a method that comprises optically resolving racemic 3-[3-(methylsulfonyl)phenyl] piperidine with optically-active tartaric acid followed by reacting the resulting product with propionaldehyde and reducing it (*Tetrahedron Letters*, Vol. 35, No. 48, 9063–9066).

However, the method of deriving the compound from optically-active 3-(3-hydroxyphenyl)-1-propylpiperidine often involves racemization as it includes multiple steps in which the compounds being processed are kept all the time optically active, and its yield to give the intended optically-active 3-[3-(methylsulfonyl)phenyl]-1-propylpiperidine of high optical purity is low.

In the method that comprises optically resolving racemic 3-[3-(methylsulfonyl)phenyl]piperidine with optically-active tartaric acid followed by deriving the intended compound from the resulting intermediate, the yield of optical resolution is low and, in addition, the optical purity of optically-active 3-[3-(methylsulfonyl)phenyl]piperidine is low.

DISCLOSURE OF THE INVENTION

The present invention is to provide a method of racemizing optically-active piperidine derivatives of optical antipodes, by-products in producing optically-active piperidine derivatives, and to provide a method of optically resolving the racemic derivatives for obtaining the necessary optically-active piperidine derivatives or their acid salts.

The constitution of the invention is as follows:

(1) A method for producing racemic piperidine derivatives, which comprises processing an optically-active piperidine derivative of any of general formulae (1), (2) and (3):

(1)

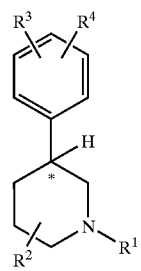

(2)

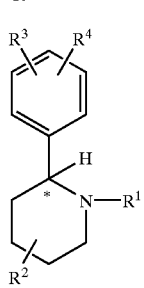

(3)

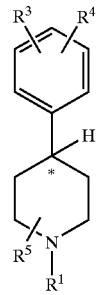

wherein $R^1$ represents a lower alkyl group having from 1 to 4 carbon atoms, a phenyl group, or an aralkyl group; $R^2$, $R^3$ and $R^4$ may be the same or different, each representing a hydrogen atom, an alkyl group, a phenyl group, an aralkyl group, an alkoxycarbonyl group, an alkylsulfonyl group, an arylsulfonyl group, an aralkylsulfonyl group, or an acyl group; $R^5$ represents an alkyl group, a phenyl group, an aralkyl group, an alkoxycarbonyl group, an alkylsulfonyl group, an arylsulfonyl group, an aralkylsulfonyl group, or an acyl group, in a hydrogen atmosphere in the presence of a reducing catalyst.

(2) The method for producing racemic piperidine derivatives of above (1), wherein the reducing catalyst contains a metal of Group VIII of the Periodic Table.

(3) The method for producing racemic piperidine derivatives of above (2), wherein the metal of Group VIII of the Periodic Table is platinum.

(4) The method for producing racemic piperidine derivatives of any one of above (1) to (3), wherein the hydrogen atmosphere is a pressure system of at least 0.2 MPa.

(5) The method for producing racemic piperidine derivatives of any of above (1) to (4), wherein the optically-active piperidine derivative is one represented by a formula (4) or (5):

(4)

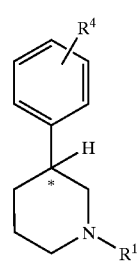

(5)

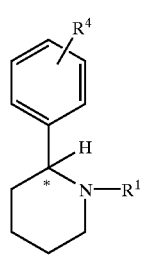

wherein $R^1$ represents a lower alkyl group having from 1 to 4 carbon atoms; and $R^4$ represents an alkylsulfonyl group having from 1 to 4 carbon atoms.

(6) The method for producing racemic piperidine derivatives of any one of above (1) to (5), wherein the optically-active piperidine derivative is optically-active 3-[3-(methylsulfonyl)phenyl]-1-propylpiperidine of a formula (6):

(6)

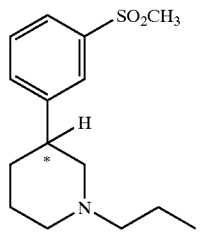

(7) A method for producing optically-active piperidine derivatives or their acid salts, which comprises optically resolving the racemic piperidine derivative obtained in any one of above (1) to (6).

(8) The method for producing optically-active piperidine derivatives or their acid salts of above (7), wherein the optically-resolving agent is an O,O'-diacyltartaric acid.

(9) The method for producing optically-active piperidine derivatives or their acid salts of above (7), wherein the optically-active O,O'-diacyltartaric acid derivative is represented by the following general formula (7):

(7)

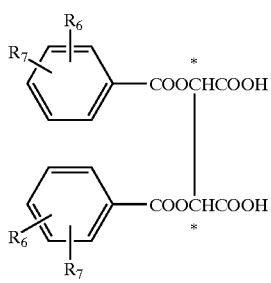

wherein $R^6$ and $R^7$ each represent a hydrogen atom, a halogen atom, an alkyl group having from 1 to 3 carbon atoms, an alkoxyl group having from 1 to 3 carbon atoms, or a nitro group, and $R^6$ and $R^7$ may be the same or different.

(10) The method for producing optically-active piperidine derivatives or their acid salts of above (9), wherein $R^6$ and $R^7$ in formula (7) each are any of a hydrogen atom, a methyl group and a methoxy group.

(11) The method for producing optically-active piperidine derivatives or their acid salts of above (10), wherein $R^6$ in formula (7) is a hydrogen atom, and $R^7$ therein is any of a hydrogen atom, a methyl group or a methoxy group.

(12) The method for producing optically-active piperidine derivatives or their acid salts of above (11), wherein the optically-active O,O'-diacyltartaric acid is any of optically-active dibenzoyltartaric acid, optically-active di-p-toluoyltartaric acid or optically-active dianisoyltartaric acid.

BEST MODE FOR CARRYING OUT THE INVENTION

The starting substances for use in the invention, optically-active piperidine derivatives are any of the following general formulae (1), (2) and (3):

(1)

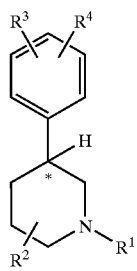

(2)

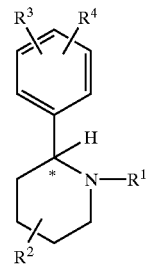

(3)

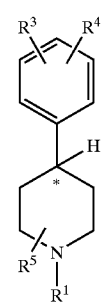

wherein $R^1$ represents a lower alkyl group having from 1 to 4 carbon atoms, a phenyl group, or an aralkyl group; $R^2$, $R^3$ and $R^4$ may be the same or different, each representing a hydrogen atom, an alkyl group, a phenyl group, an aralkyl group, an alkoxycarbonyl group, an alkylsulfonyl group, an arylsulfonyl group, an aralkylsulfonyl group, or an acyl group; $R^5$ represents an alkyl group, a phenyl group, an aralkyl group, an alkoxycarbonyl group, an alkylsulfonyl group, an arylsulfonyl group, an aralkylsulfonyl group, or an acyl group. Of those, preferred for racemization are optically-active piperidine derivatives of formula (1) or (2); and more preferred are optically-active piperidine derivatives of the following general formula (4) or (5):

(4)

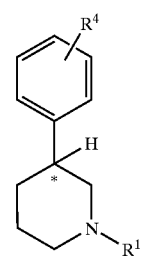

(5)

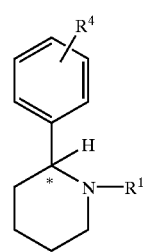

wherein $R^1$ represents a lower alkyl group having from 1 to 4 carbon atoms; and $R^4$ represents an alkylsulfonyl group having from 1 to 4 carbon atoms.

In particular, the invention is especially favorable for producing racemic 3-[3-(methylsulfonyl)phenyl]-1-propylpiperidine of a formula (6):

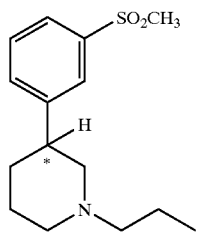

(6)

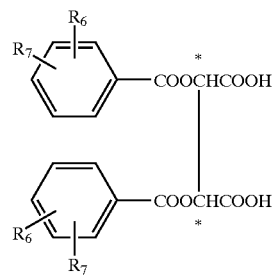

(7)

The optically-active piperidine derivative referred to herein is meant to indicate a piperidine derivative of which the amount of one optical isomer is larger than that of the other optical isomer, substantially indicating such a piperidine derivative having an optical purity of at least 30% e.e.

The racemic piperidine derivative also referred to herein is meant to indicate a piperidine derivative of which the optical purity is lower than that of the starting compound for it, substantially indicating such a piperidine derivative having an optical purity of lower than 30% e.e.

The racemization in the invention may be effected in the absence of a solvent, but is preferably effected in an inert organic solvent. Concretely, any of hydrocarbons such as benzene, toluene, xylene, hexane, octane, decane, cyclohexane; alcohols such as methanol, ethanol, propanol, isopropanol, butanol, isobutanol, t-butanol; ethers such as ethyl ether, isopropylether, butylether, isobutyl ether, tetrahydrofuran, dioxane; or their mixed solvents may be used for the reaction solvent. These solvents may contain water. The amount of the solvent for use herein is not specifically defined, but is preferably at most 50 times by volume relative to the substrate from the economical viewpoint.

The reducing catalyst for use in the invention is preferably a catalyst that contains a noble metal of Group VIII of the Periodic Table, such as nickel, cobalt, ruthenium, rhodium, palladium or platinum, more preferably a catalyst that contains platinum. Its morphology is not specifically defined. For example, herein usable are Raney catalysts such as Raney nickel, Raney cobalt; and catalysts of ruthenium, rhodium, palladium or platinum held on activated charcoal, alumina or asbestos. These catalysts may be used either singly or as combined. The amount of the catalyst to be used is not specifically defined, but preferably falls between 0.01 and 0.5 times by weight relative to the optically-active piperidine derivative to be processed with it.

The reaction is effected preferably at a temperature not lower than 100° C., more preferably not lower than 150° C.; and the hydrogen pressure for the reaction is preferably at least 0.2 MPa. The time for racemization depends on the reaction temperature, the hydrogen pressure, the type of the catalyst used and the amount of the catalyst used, generally falling between 5 and 40 hours.

The intended product, racemic piperidine derivative racemized herein may be taken out by concentrating the filtrate of the reaction mixture from which the catalyst has been removed through filtration after the reaction.

Thus obtained herein, the racemic piperidine derivatives are usable as the starting materials for diastereomer salt resolution.

The optically-resolving agent for use in the invention is selected from optically-active O,O'-diacyltartaric acids, of which the D-forms and the L-forms may be selectively used herein in accordance with the object of the invention.

For the optically-active O,O'-diacyltartaric acids, for example, compounds of the following general formula (7) are usable.

wherein $R^6$ and $R^7$ each represent a hydrogen atom, a halogen atom, an alkyl group having from 1 to 3 carbon atoms, an alkoxyl group having from 1 to 3 carbon atoms, or a nitro group, and $R^6$ and $R^7$ may be the same or different.

Of such O,O'-diacyltartaric acids of formula (7), preferred for use herein are those in which $R^6$ and $R^7$ each are any of a hydrogen atom, a methyl group and a methoxy group, and more preferred are those in which $R^6$ is a hydrogen atom and $R^7$ is any of a hydrogen atom, a methyl group or a methoxy group. Concretely, for example, they include optically-active dibenzoyltartaric acid, optically-active di-p-toluoyltartaric acid, optically-active dianisoyltartaric acid and their hydrates.

These optically-active tartaric acid derivatives may be readily produced from optically-active tartaric acid in any known method.

The starting material in the invention, racemic piperidine derivative may be not only a 50/50 mixture of S-form and R-form isomers but also any other mixtures in which the amount of any one of the optical isomers is larger than that of the other one.

The starting racemic piperidine derivative is brought into contact with from 0.4 to 1.5 mols, but preferably from 0.7 to 1.2 mols, relative to the starting racemic piperidine derivative, of such an optically-active O,O'-diacyltartaric acid in a solvent to give a diastereomer salt. If desired, an organic carboxylic acid such as formic acid, acetic acid or propionic acid may be present in the reaction system. The amount of the organic carboxylic acid that may be in the system may fall between 0.8 and 1.5 mols, but preferably between 0.9 and 1.2 mols, relative to one mol of the racemic piperidine derivative and in terms of the sum total of the acid and the optically-resolving agent used in the system.

The solvent to be in the system may be any and every one not chemically degrading both the piperidine derivative and the optically-resolving agent in the solution containing them, but having the ability to precipitate any one diastereomer salt formed therein. For it, for example, usable are any of water; alcohols such as methanol, ethanol, 1-propanol, 2-propanol, 1-butanol, 2-butanol, tert-butanol; ketones such as acetone, methyl ethyl ketone; other organic solvents such as acetonitrile, tetrahydrofuran, 1,4-dioxane, 1,3-dioxolane, chloroform, chlorobenzene; and their mixed solvents.

Regarding the mode of contacting the racemic piperidine derivative with the optically-resolving agent, both the racemic piperidine derivative and the optically-resolving agent may be added to the solvent all at a time, or they may be added thereto one after another. In case where an organic carboxylic acid is present in the reaction system, they may be added to the solvent all at a time, or may be added thereto one after another. The order of adding them to the solvent is not specifically defined.

The solution that contains the diastereomer salts thus formed therein is cooled and/or concentrated, whereby one diastereomer salt hardly soluble in the solution is precipitated therein.

The temperature at which the hardly-soluble diastereomer salt is precipitated in the solution may fall between the freezing point and the boiling point of the solvent used, and may be suitably determined in accordance with the object of the invention. Generally, the preferred range of the temperature falls between −20° C. and 50° C.

The crystal of the hardly-soluble diastereomer salt may be readily separated in any ordinary solid-liquid separation such as filtration or centrifugation. Thus separated, the hardly-soluble diastereomer salt crystal may be subjected to recrystallization or re-slurry washing to be the intended diastereomer salt of high purity.

Thus obtained, the diastereomer salt is desalted in any suitable manner, whereby the intended optically-active piperidine derivative may be separated from the optically-resolving agent and the two may be separately collected.

Desalting the diastereomer salt may be effected in any known manner, for which, for example, employable is a method of processing the salt with an acid or alkali in an aqueous solvent or a method of processing it with an ion-exchange resin. Concretely, the diastereomer salt is desalted in an aqueous solution of an alkali such as sodium hydroxide in water, and then extracted with an organic solvent such as isopropyl ether. Through the process, the desalted piperidine derivative is extracted out in the organic phase, and the resulting extract is concentrated to obtain the intended, optically-active piperidine derivative. Next, a mineral acid such as hydrochloric acid or sulfuric acid is added to the aqueous phase from which the piperidine derivative has been removed so that the aqueous phase may have a pH of from 1 to 2, and the optically-resolving agent thus precipitated in the resulting aqueous phase is taken out through filtration. Alternatively, the optically-resolving agent in the aqueous phase is extracted with an organic solvent such as dichloromethane. In that manner, the optically-resolving agent is collected.

Thus obtained, the optically-active piperidine derivative is reacted with a mineral acid such as hydrochloric acid or sulfuric acid or with an organic acid such as formic acid, acetic acid or propionic acid to give an acid salt of the piperidine derivative.

The optically-active 3-[3-(methylsulfonyl)phenyl]-1-propylpiperidine is useful for medicines.

EXAMPLES

The invention is described in more detail with reference to the following Examples, which, however, are not intended to restrict the scope of the invention.

The optical purity of 3-[3-(methylsulfonyl)phenyl]-1-propylpiperidine obtained in the Examples was obtained according to the following method: From 8 to 10 mg of 3-[3-(methylsulfonyl)phenyl]-1-propylpiperidine is dissolved in 10 ml of an n-hexane solution that contains 25% ethanol, and 20 µl of the resulting solution is analyzed through HPLC. The column used for the analysis is Chiralpak AS (Daicel); and the mobile phase is isohexane/methanol/diethylamine=97.5/2.5/0.1 (v/v/v). The column temperature is about 25° C.; the flow rate is 0.60 ml/min; and UV (267 nm) is used for detection. (R)-3-[3-(methylsulfonyl)phenyl]-1-propylpiperidine is detected in 24.5 minutes, and (S)-3-[3-(methylsulfonyl)phenyl]-1-propylpiperidine is detected in 26.1 minutes.

Example 1

0.49 g of (R)-3-[3-(methylsulfonyl)phenyl]-1-propylpiperidine (optical purity, 61% e.e.), 0.20 g of 5% platinum/activated charcoal (wet) and 5 ml of ethanol were put in to a 100-ml autoclave, and processed therein under a hydrogen pressure of 0.5 MPa and at a temperature of 180° C. for 21 hours. After the reaction, the autoclave was cooled and opened, and the reaction mixture therein was filtered to remove the catalyst. The resulting filtrate was concentrated to obtain 0.52 g of pale yellow oil. Its optical purity was 0% e.e., and the degree of racemization in this process was 100%.

Example 2

0.53 g of (R)-3-[3-(methylsulfonyl)phenyl]-1-propylpiperidine (optical purity, 61% e.e.), 0.20 g of 5% platinum/activated charcoal (wet) and 5 ml of ethanol were put in to a 100-ml autoclave, and processed therein under a hydrogen pressure of 1.0 MPa and at a temperature of 180° C. for 21 hours. After the reaction, the autoclave was cooled and opened, and the reaction mixture therein was filtered to remove the catalyst. The resulting filtrate was concentrated to obtain 0.53 g of pale yellow oil. Its optical purity was 0% e.e., and the degree of racemization in this process was 100%.

Example 3

0.50 g of (R)-3-[3-(methylsulfonyl)phenyl]-1-propylpiperidine (optical purity, 61% e.e.), 0.20 g of 5% platinum/activated charcoal (wet) and 5 ml of n-propanol were put into a 100-ml autoclave, and processed therein under a hydrogen pressure of 1.0 MPa and at a temperature of 180° C. for 18 hours. After the reaction, the autoclave was cooled and opened, and the reaction mixture therein was filtered to remove the catalyst. The resulting filtrate was concentrated to obtain 0.50 g of pale yellow oil. Its optical purity was 0% e.e., and the degree of racemization in this process was 100%.

Example 4

35 g of (R)-3-[3-(methylsulfonyl)phenyl]-1-propylpiperidine (optical purity, 61% e.e.), 14 g of 5% platinum/activated charcoal (wet) and 350 ml of n-propanol were put into a 500-ml autoclave, and processed therein under a hydrogen pressure of 1.0 MPa and at a temperature of 180° C. for 19 hours. After the reaction, the autoclave was cooled and opened, and the reaction mixture therein was filtered to remove the catalyst. The resulting filtrate was concentrated to obtain 36.5 g of pale yellow oil. Its optical purity was 0% e.e., and the degree of racemization in this process was 100%.

Example 5

0.49 g of (R)-3-[3-(methylsulfonyl)phenyl]-1-propylpiperidine (optical purity, 61% e.e.), 0.20 g of 5% platinum/activated charcoal (wet) and 5 ml of n-butanol were put into a 100-ml autoclave, and processed therein under a hydrogen pressure of 1.0 MPa and at a temperature of 180° C. for 21 hours. After the reaction, the autoclave was cooled and opened, and the reaction mixture therein was filtered to remove the catalyst. The resulting filtrate was concentrated to obtain 0.52 g of pale yellow oil. Its optical purity was 0% e.e., and the degree of racemization in this process was 100%.

Example 6

0.53 g of (R)-3-[3-(methylsulfonyl)phenyl]-1-propylpiperidine (optical purity, 61% e.e.), 0.20 g of 5% ruthenium/activated charcoal (wet) and 5 ml of ethanol were put into a 100-ml autoclave, and processed therein under a hydrogen pressure of 1.0 MPa and at a temperature of 180° C. for 21 hours. After the reaction, the autoclave was cooled and opened, and the reaction mixture therein was filtered to remove the catalyst. The resulting filtrate was concentrated to obtain 0.57 g of pale yellow oil. Its optical purity was 43% e.e., and the degree of racemization in this process was 30%.

Example 7

0.52 g of (R)-3-[3-(methylsulfonyl)phenyl]-1-propylpiperidine (optical purity, 61% e.e.), 0.20 g of 5% rhodium/activated charcoal (wet) and 5 ml of ethanol were put into a 100-ml autoclave, and processed therein under a hydrogen pressure of 1.0 MPa and at a temperature of 180° C. for 21 hours. After the reaction, the autoclave was cooled and opened, and the reaction mixture therein was filtered to remove the catalyst. The resulting filtrate was concentrated to obtain 0.55 g of pale yellow oil. Its optical purity was 46% e.e., and the degree of racemization in this process was 25%.

Example 8

0.53 g of (R)-3-[3-(methylsulfonyl)phenyl]-1-propylpiperidine (optical purity, 61% e.e.), 0.20 g of Raney nickel (wet) and 5 ml of ethanol were put into a 100-ml autoclave, and processed therein under a hydrogen pressure of 1.0 MPa and at a temperature of 180° C. for 21 hours. After the reaction, the autoclave was cooled and opened, and the reaction mixture therein was filtered to remove the catalyst. The resulting filtrate was concentrated to obtain 0.56 g of pale yellow oil. Its optical purity was 58% e.e., and the degree of racemization in this process was 5%.

Example 9

0.51 g of (R)-3-[3-(methylsulfonyl)phenyl]-1-propylpiperidine (optical purity, 61% e.e.), 0.20 g of 5% platinum/activated charcoal (wet) and 5 ml of toluene were put into a 100-ml autoclave, and processed therein under a hydrogen pressure of 1.0 MPa and at a temperature of 150° C. for 20 hours. After the reaction, the autoclave was cooled and opened, and the reaction mixture therein was filtered to remove the catalyst. The resulting filtrate was concentrated to obtain 0.53 g of pale yellow oil. Its optical purity was 57% e.e., and the degree of racemization in this process was 7%.

Example 10

0.51 g of (R)-3-[3-(methylsulfonyl)phenyl]-1-propylpiperidine (optical purity, 61% e.e.), 0.20 g of 5% platinum/activated charcoal (wet) and 5 ml of isopropyl ether were put into a 100-ml autoclave, and processed therein under a hydrogen pressure of 1.0 MPa and at a temperature of 150° C. for 20 hours. After the reaction, the autoclave was cooled and opened, and the reaction mixture therein was filtered to remove the catalyst. The resulting filtrate was concentrated to obtain 0.54 g of pale yellow oil. Its optical purity was 55% e.e., and the degree of racemization in this process was 10%.

Example 11

3.7 g of (R)-3-[3-(methylsulfonyl)phenyl]-1-propylpiperidine (optical purity, 50% e.e.), 1.6 g of 5% platinum/activated charcoal (wet) and 40 ml of ethanol were put into a 100-ml autoclave, and processed therein under a hydrogen pressure of 1.0 MPa and at a temperature of 180° C. for 18 hours. After the reaction, the autoclave was cooled and opened, and the reaction mixture therein was filtered to remove the catalyst. The resulting filtrate was concentrated to obtain 4.0 g of pale yellow oil. Its optical purity was 0% e.e., and the degree of racemization in this process was 100%.

Example 12

11.00 g of the racemic 3-[3-(methylsulfonyl)phenyl]-1-propylpiperidine obtained in the process of Example 4 (purity, 94.0%; 36.7 mmols), 16.18 g (40.0 mmols) of di-p-toluoyl-D-tartaric acid monohydrate and 150 ml of acetonitrile were put into a 200-ml flask, and heated at 40° C. to form a uniform solution. The solution was cooled to 20° C., and 50 mg of (R)-3-[3-(methylsulfonyl)phenyl]-1-propylpiperidine di-p-toluoyl-D-tartrate was added thereto and then stirred at 18 to 22° C. for 7 hours. The resulting precipitate was taken out through filtration and then dried to obtain 7.70 g of (R)-3-[3-(methylsulfonyl)phenyl]-1-propylpiperidine di-p-toluoyl-D-tartrate. In the crystal, the content of 3-[3-(methylsulfonyl)phenyl]-1-propylpiperidine was 41.3%, and the optical purity thereof was 90.6% e.e.

Example 13

11.05 g of the racemic 3-[3-(methylsulfonyl)phenyl]-1-propylpiperidine obtained in the process of Example 4 (purity, 94.0%; 36.9 mmols), 16.18 g (40.0 mmols) of di-p-toluoyl-L-tartaric acid monohydrate and 150 ml of acetonitrile were put into a 200-ml flask, and heated at 40° C. to form a uniform solution. The solution was cooled to 20° C., and 50 mg of (S)-3-[3-(methylsulfonyl)phenyl]-1-propylpiperidine di-p-toluoyl-L-tartrate was added thereto and then stirred at 18 to 20° C. for 9 hours. The resulting precipitate was taken out through filtration and then dried to obtain 10.05 g of (S)-3-[3-(methylsulfonyl)phenyl]-1-propylpiperidine di-p-toluoyl-L-tartrate. In the crystal, the content of 3-[3-(methylsulfonyl)phenyl]-1-propylpiperidine was 41.8%, and the optical purity thereof was 90.8% e.e.

Example 14

11.02 g of the racemic 3-[3-(methylsulfonyl)phenyl]-1-propylpiperidine obtained in the process of Example 4 (purity, 92.8%; 36.3 mmols), 15.06 g (40.4 mmols) of dibenzoyl-D-tartaric acid monohydrate and 85 ml of acetonitrile were put into a 100-ml flask, and stirred at about 30° C. to form a uniform solution. The solution was cooled to 3° C., and 50 mg of (S)-3-[3-(methylsulfonyl)phenyl]-1-propylpiperidine dibenzoyl-D-tartrate was added thereto and then stirred at 0 to 3° C. for 23 hours. The resulting precipitate was taken out through filtration and then dried to obtain 8.67 g of (S)-3-[3-(methylsulfonyl)phenyl]-1-propylpiperidine dibenzoyl-D-tartrate. In the crystal, the content of 3-[3-(methylsulfonyl)phenyl]-1-propylpiperidine was 41.3%, and the optical purity thereof was 88.0% e.e.

Example 15

11.08 g of the racemic 3-[3-(methylsulfonyl)phenyl]-1-propylpiperidine obtained in the process of Example 4 (purity, 92.8%; 36.5 mmols), 16.73 g (40.0 mmols) of dianisoyl-D-tartaric acid and 200 ml of acetonitrile were put into a 300-ml flask, and heated at 50° C. to form a uniform solution. The solution was cooled to 30° C., and stirred at 27 to 30° C. for 3 hours. The resulting precipitate was taken out through filtration and then dried to obtain 11.99 g of (S)-3-[3-(methylsulfonyl)phenyl]-1-propylpiperidine dianisoyl-D-tartrate. In the crystal, the content of 3-[3-

(methylsulfonyl)phenyl]-1-propylpiperidine was 38.8%, and the optical purity thereof was 92.3% e.e.

INDUSTRIAL APPLICABILITY

According to the present invention, racemic piperidine derivatives are efficiently obtained in an industrial process. Using the optically-resolving agent of the invention enables a high yield of optically-active piperidine derivatives or their acid salts of high optical purity. These are usable for medicines or their intermediates.

What is claimed is:

1. A method for producing racemic piperidine derivatives, which comprises processing an optically-active piperidine derivative of any of general formulae (1), (2) and (3):

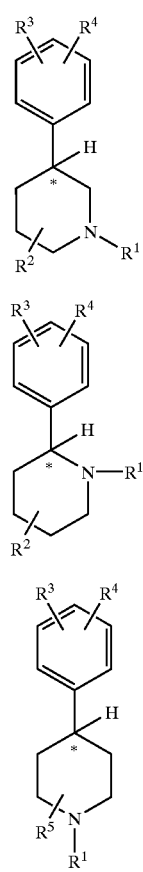

wherein $R^1$ represents a lower alkyl group having from 1 to 4 carbon atoms, a phenyl group, or an aralkyl group; $R^2$, $R^3$ and $R^4$ may be the same or different, each representing a hydrogen atom, an alkyl group, a phenyl group, an aralkyl group, an alkoxycarbonyl group, an alkylsulfonyl group, an allylsulfonyl group, an aralkylsulfonyl group, or an acyl group; $R^5$ represents an alkyl group, a phenyl group, an aralkyl group, an alkoxycarbonyl group, an alkylsulfonyl group, an allylsulfonyl group, an aralkylsulfonyl group, or an acyl group, in a hydrogen atmosphere in the presence of a reducing catalyst.

2. The method for producing racemic piperidine derivatives as claimed in claim 1, wherein the reducing catalyst contains a metal of Group VIII of the Periodic Table.

3. The method for producing racemic piperidine derivatives as claimed in claim 2, wherein the metal of Group VIII of the Periodic Table is platinum.

4. The method for producing racemic piperidine derivatives as claimed in any one of claims 1 to 3, wherein the hydrogen atmosphere is a pressure system of at least 0.2 MPa.

5. The method for producing racemic piperidine derivatives as claimed in claim 1, wherein the optically-active piperidine derivative is one represented by a formula (4) or (5):

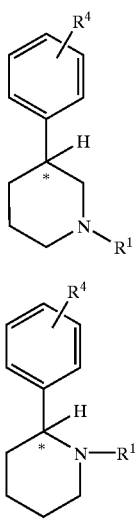

wherein $R^1$ represents a lower alkyl group having from 1 to 4 carbon atoms; and $R^4$ represents an alkylsulfonyl group having from 1 to 4 carbon atoms.

6. The method for producing racemic piperidine derivatives as claimed in claim 1, wherein the optically-active piperidine derivative is optically-active 3-[3-(methylsulfonyl)phenyl]-1-propylpiperidine of a formula (6):

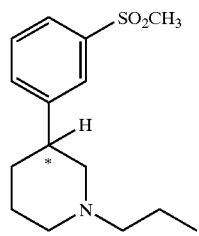

* * * * *

UNITED STATES PATENT AND TRADEMARK OFFICE
CERTIFICATE OF CORRECTION

PATENT NO. : 6,962,998 B2  Page 1 of 1
APPLICATION NO. : 10/296772
DATED : November 8, 2005
INVENTOR(S) : Fujino et al It is certified that error appears in the above-identified patent and that said Letters Patent is hereby corrected as shown below:

Title Page
At (73), change "Toray Industries, Inc." to --Toray Fine Chemicals Co., Ltd.--

Signed and Sealed this

Eighth Day of August, 2006

JON W. DUDAS
*Director of the United States Patent and Trademark Office*